United States Patent
Chevalier et al.

(10) Patent No.: US 6,643,014 B2
(45) Date of Patent: *Nov. 4, 2003

(54) METHOD AND A SYSTEM FOR IDENTIFYING GASEOUS EFFLUENTS, AND A FACILITY PROVIDED WITH SUCH A SYSTEM

(75) Inventors: Eric Chevalier, Annecy le Vieux (FR); Philippe Maquin, St Jean de Sixt (FR); Roland Bernard, Viuz-la-Chiesaz (FR)

(73) Assignee: Alcatel, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/487,722

(22) Filed: Jan. 19, 2000

(65) Prior Publication Data

US 2003/0160956 A1 Aug. 28, 2003

(30) Foreign Application Priority Data

Jan. 22, 1999 (FR) .............................. 99 00723

(51) Int. Cl.$^7$ .............................................. G01N 21/73
(52) U.S. Cl. ......................................... 356/316; 356/72
(58) Field of Search ................... 356/72, 316

(56) References Cited

U.S. PATENT DOCUMENTS

| | | | | |
|---|---|---|---|---|
| 3,521,959 A | * | 7/1970 | Fassel et al. ............ | 356/316 |
| 3,843,257 A | | 10/1974 | Wooten | |
| 3,958,883 A | * | 5/1976 | Turner .................. | 356/316 |
| 4,136,951 A | * | 1/1979 | Macourt ............... | 356/316 |
| 4,629,887 A | * | 12/1986 | Bernier ................. | 356/316 |
| 4,857,136 A | * | 8/1989 | Zajac ..................... | 216/60 |
| 4,902,099 A | * | 2/1990 | Okamoto et al. ..... | 356/316 |
| 5,825,485 A | | 10/1998 | Cohn et al. | |
| 5,986,747 A | * | 11/1999 | Moran .................. | 356/316 |
| 6,366,346 B1 | * | 4/2002 | Nowak et al. ........ | 356/72 |

FOREIGN PATENT DOCUMENTS

| | | |
|---|---|---|
| DE | 195 05 104 A1 | 8/1996 |
| DE | 195 44 506 A1 | 6/1997 |
| WO | WO 97/13141 | 4/1997 |

OTHER PUBLICATIONS

"The Physics of Inductively Coupled Plasma Sources," Amy E. Wendt, 1997, pp. 435–442.

* cited by examiner

Primary Examiner—F. L. Evans
(74) Attorney, Agent, or Firm—Sughrue Mion, PLLC

(57) ABSTRACT

The invention relates to a gas analysis system for analyzing gases in an enclosure under controlled pressure, which system comprises apparatus for ionizing the gases to be analyzed, and apparatus for analyzing the ionized gases. According to the invention the apparatus for ionizing the gases to be analyzed comprises a dedicated plasma source in contact with the gases contained in the enclosure and combined with a generator for generating a plasma from the gases to be analyzed; and the apparatus for analyzing the ionized gases comprises a radiation sensor situated in the vicinity of the zone in which the plasma is generated, and connected to an optical spectrometer for analyzing the variation of the radiation spectrum emitted by the generated plasma.

15 Claims, 2 Drawing Sheets

METHOD AND A SYSTEM FOR IDENTIFYING GASEOUS EFFLUENTS, AND A FACILITY PROVIDED WITH SUCH A SYSTEM

The invention relates to a method and a system for analyzing gaseous effluents. More particularly, the invention relates to a method and a system for analyzing gaseous effluents in an enclosure under a controlled pressure. The invention also relates to an industrial facility including at least one controlled-pressure enclosure and a system for analyzing the gases contained in the controlled-pressure enclosure.

BACKGROUND OF THE INVENTION

The progress made in recent years in the semiconductor industry is essentially related to the integration of electronic circuits on components of a few square millimeters; this being done on silicon substrates that are increasingly large (diameter in the range 200 mm to 300 mm).

The number of technological steps necessary to make such circuits is large (up to 400).

Among such steps, the vacuum treatment steps are of essential importance both by their ability to produce continuously throughout the manufacturing process and also by their functions of satisfying the geometrical criteria of the component.

installing an in situ analysis system identifies defects as soon as they occur, thereby reducing the reaction time during which a large number of batches can be produced.

As a result, a high demand is emerging for in situ and real time monitoring and controlling of plasma semiconductor manufacturing processes performed in a vacuum.

That demand is becoming stronger not only in the chambers in which the various steps are performed but also on the various components constituting the pumping lines.

Among the in situ inspection steps, the analysis of organic elements, particles, mold, metal ions, and any gases in gaseous form or at the condensation limit is important because it makes it possible:

to determine whether the optimum manufacturing conditions are satisfied; for example, an in situ analysis performed in the vacuum pumping system, upstream from the process chamber makes it possible to control the environment of the silicon wafers better, thereby improving production yields; and to estimate the ageing of the mechanical components making up the machine, and thus, by means of predictive maintenance, to manage the maintenance schedule of the machine effectively by preempting incidents.

The problem encountered in implementing a gas analysis technique lies in the investment cost and the saving achieved by preventive detection of defects in comparison with the production costs and the quality costs generated by the processes.

In addition, the gas analysis system must be increasingly small in order to take account of the pumping systems being integrated in semiconductor facilities.

A gas analyzer operating in the range 0.1 mbars to 1000 mbars would make it possible to monitor reactive species during the process steps, and to do so all the way to the outlet of the vacuum facility, thereby improving the monitoring of the gases released into the atmosphere.

As is known, residual gas analysis (RGA) by mass spectrometry makes it possible to detect all inert and charged gaseous species. The molecules are usually ionized in an ionization chamber by electrons delivered by thermionic emission from a hot filament. That technology is applicable for pressures lower than $10^{-6}$ mbars, above $10^{-5}$ mbars the response becomes non-linear, and above $10^{-4}$ mbars the filament can be destroyed.

For analyzing gases in the desired range (0.1 mbars to 1000 mbars), it is necessary to set up differential pumping so as to reduce the pressure inside the analysis unit, in order to avoid destroying the filament. This differential pumping apparatus comprises a plurality of vacuum pumps and numerous valves.

Since a plurality of vacuum pumps and valves are used, the cost of a gas analyzer operating at high pressures (0.1 mbars to 1000 mbars) is six times higher than an RGA-type analyzer which analyzes the residual vacuum only; and thus its cost is dissuasive compared with the cost of the semiconductor manufacturing machine and with the quantitative and qualitative efficiency thereof.

In addition, the space occupied by a mass gas analyzer with differential pumping is large because such an analyzer incorporates several voluminous vacuum components. That makes it difficult to integrate into current vacuum facilities which often comprise several manufacturing chambers.

That is why few vacuum facilities are equipped with gas analyzers in spite of demand from industry.

The use of optical emission spectroscopy is also known in facilities for manufacturing semiconductors. Emission spectrometry is used to detect the end of etching in processes for etching semiconductor components or circuits. The plasma analyzed is the plasma generated by the reactor of the facility, having instruments which merely comprise an emission spectrometer which analyzes the light from the etching process, making it possible to monitor the steps of the process itself.

OBJECTS AND SUMMARY OF THE INVENTION

An object of the invention is to use optical emission spectrometry to monitor all of the gaseous components of the vacuum environment of the facility, rather than to monitor the steps of the manufacturing or etching process of the semiconductor facility.

To this end, the invention provides a gas analysis system for analyzing gases in an enclosure under controlled pressure, which system comprises apparatus for ionizing the gases to be analyzed, and apparatus for analyzing the ionized gases.

According to the invention:

the apparatus for ionizing the gases to be analyzed comprises a dedicated plasma source in contact with the gases contained in the enclosure and combined with a generator for generating a plasma from the gases to be analyzed; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

The plasma source may be a microwave source of the resonant cavity type, or of the type using the surface wave propagation principle.

An alternative would be to use a radiofrequency plasma source of the inductively coupled plasma (ICP) type. Such a source requires a dielectric made of quartz or of alumina (depending on the chemical nature of the effluents: fluorine-containing gases react strongly with quartz) which dielectric provides sealing and is transparent to electromagnetic waves.

The radiation sensor may be an optical fiber serving to pick up the radiation spectrum emitted by the generated plasma and to convey it towards the optical spectrometer.

In a first embodiment, the analysis system is integrated in series in a pipe in which the gaseous effluents are to be monitored.

In an alternative embodiment, the analysis system is mounted on a pipe via an external coupling.

The invention also provides a facility including at least one controlled-pressure enclosure, and a gas analysis system for analyzing the gases contained in the controlled-pressure enclosure.

According to the invention, the gas analysis system is as defined above.

Each of the sources makes it possible to generate plasma from the gases existing in the enclosure, to do so while the facility is in operation, and to do so from low pressures up to atmospheric pressure.

The ionization efficiency obtained by these types of plasma source is close to 10% for a pressure of $10^{-1}$ mbars, hence very high measurement accuracy is achieved.

After diffracting the light, the optical spectrometer analyzes, in real time, the variations of radiation emitted by the atoms, molecules, and ions, when exited by the free electrons of the plasma.

Thus, the combined use of a plasma source that can operate at atmospheric pressure together with an optical emission spectrum analysis system, makes it possible to obtain continuous diagnosis of the gases situated inside a controlled-pressure enclosure.

The use of differential pumping is not necessary to the operation of the ionization source, and this reduces the volume of the gas analyzer, and therefore it can be integrated easily into the semiconductor facility (in series or via a standard coupling).

Finally, the cost of this optical analysis technique is low because it associates only one ionization source with an optical detector. This facilitates generalizing it on the vacuum lines of facilities used in the semiconductor industry.

BRIEF DESCRIPTION OF THE DRAWINGS

Other advantages and characteristics of the present invention appear from the following description given with reference to the accompanying drawings, in which.

MORE DETAILED DESCRIPTION

Figure 1:
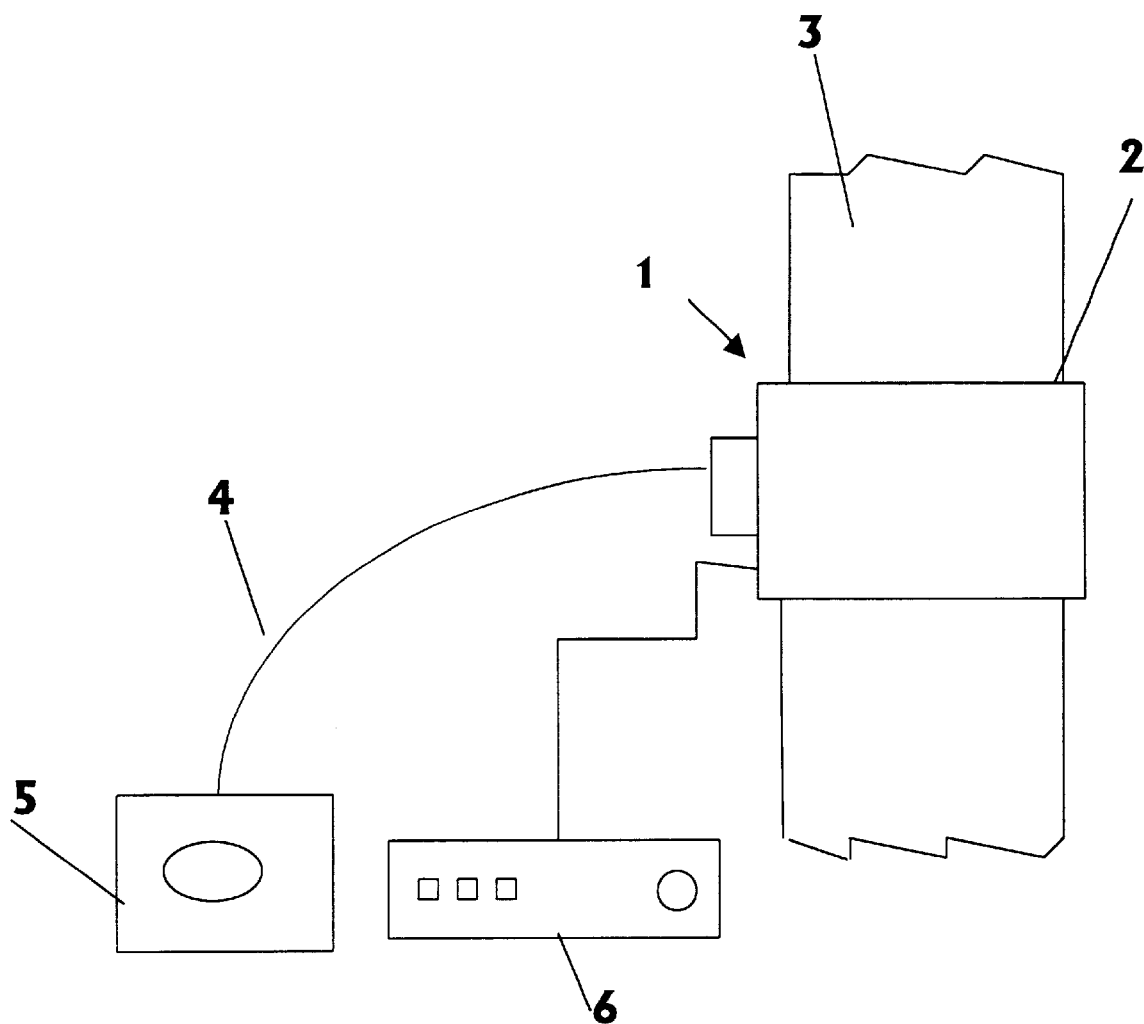
FIG. 1 is a diagram of a first connection configuration of a system of the present invention.

The gas analysis system 1 of the invention serves to analyze gaseous effluents contained in an enclosure 3 under controlled pressure. For example, the enclosure 3 may be a vacuum line 3 of a facility (not shown) for manufacturing semiconductor integrated circuits.

The operating principle of the gas analysis system 1 is based on ionizing the gases and on analyzing the radiation spectrum resulting from ionizing the gases.

For this purpose, the gas analysis system 1 includes apparatus for ionizing the gases to be analyzed, which apparatus is constituted by a dedicated plasma source 2 in contact with the gases in the enclosure 3, and generating a plasma from the gases to be analyzed. The plasma source 2 is powered by a generator 6 suited to the chosen type of plasma source 2.

In an embodiment, the plasma source 2 is a microwave source of the resonant cavity type or of the type using the surface wave propagation principle. in which case, the generator 6 is a microwave generator.

In another embodiment, the plasma source 2 is a radiofrequency (RF) plasma source of the inductively coupled plasma (ICP) type. In which case, the generator 6 is an RF generator.

To analyze the plasma, the gas analysis system 1 of the invention includes ionized gas analysis apparatus 4, 5 of the optical spectrometer type having a probe 4 situated in the vicinity of the dedicated plasma source 2 and analyzing variations in the radiation spectrum emitted by the generated plasma. The ionized gas analysis apparatus 4, 5 includes a probe optical fiber 4 having one end situated in the vicinity of the plasma source 2, inside the analyzed enclosure 3, and having its other end connected to an optical emission spectrometer 5. The radiation emitted by the atoms, molecules, and ions as excited by the free electrons of the plasma is transmitted to the optical emission spectrometer 5 via the optical fiber 4. The optical emission spectrometer 5 analyzes variations in the radiation and deduces therefrom information relating to the components of the ionized gases.

FIG. 1 is a diagram of a system 1 of the invention, as integrated in series in a pipe 3 in which the gaseous effluents are to be monitored.

Figure 2:
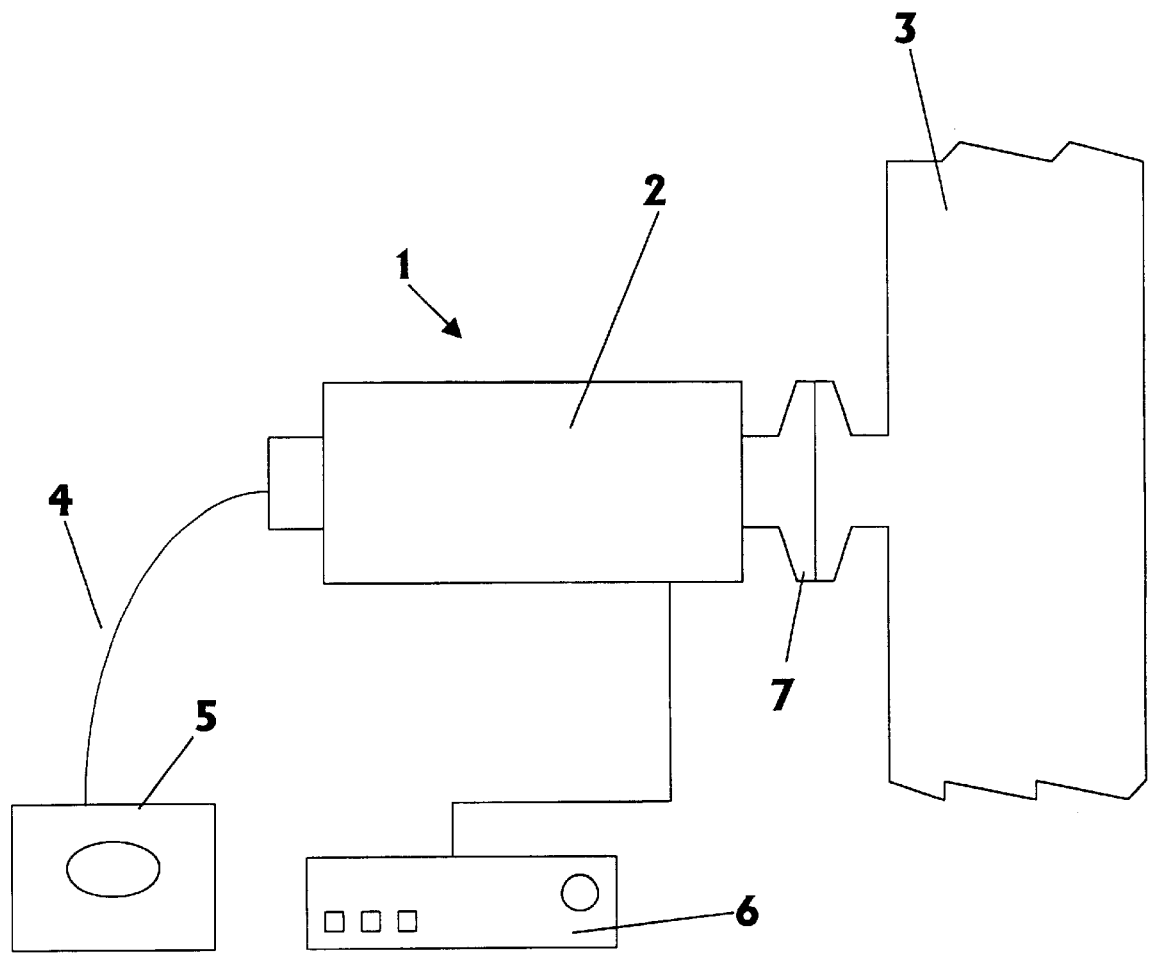
FIG. 2 is a diagram of a second connection configuration of a system of the present invention.

In another connection configuration shown in FIG. 2, the system 1 of the invention may be mounted on the pipe 3 via an external coupling 7.

Naturally, the invention is not limited to the embodiments described, but rather numerous variants are accessible to the person skilled in the art without going beyond the invention. In particular, any solution for generating plasma may be used in place of those described.

What is claimed is:

1. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, inside the vacuum pumping line, in contact with the gases contained in the vacuum pumping line, and a generator for generating a plasma from the gases to be analyzed, further wherein the plasma source is a microwave source of the resonant cavity type; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

2. The gas analysis system of claim 1 wherein the vacuum pumping line is upstream of the process chamber.

3. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, mounted to the vacuum pumping line via an external coupling and in direct contact with the gases contained in the vacuum pumping line, and a generator for generating a plasma from the gases to be analyzed, further wherein the plasma source is a microwave source of the resonant cavity type; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

4. The gas analysis system of claim 3, wherein the vacuum pumping line is upstream of the process chamber.

5. The gas analysis system of claim 3, wherein there is no valve between the apparatus for ionizing and the vacuum pumping line.

6. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, in contact with the gases contained in the vacuum pumping line, and a generator for generating a plasma from the gases to be analyzed, further wherein the plasma source is configured and arranged to generate plasma from the gas existing in the vacuum pumping line from a pressure of about $10^{-6}$ mbar up to atmospheric pressure; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

7. The gas analysis system of claim 6 wherein the vacuum pumping line is upstream of the process chamber.

8. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, in contact with the gases contained in the vacuum pumping line, and a generator for generating a plasma from the gases to be analyzed, further wherein the gas analyzer operates in the pressure range of 0.1 mbars to 1000 mbars; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

9. The gas analysis system of claim 8 wherein the vacuum pumping line is upstream of the process chamber.

10. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, inside the vacuum pumping line and in contact with the gases contained in the vacuum pumping line, and a generator for generating a plasma from the gases to be analyzed, further wherein the plasma source is a radio frequency plasma source of the inductively coupled plasma type; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

11. The gas analyzing system of claim 10, wherein the radiation sensor is an optical fiber serving to pick up the radiation spectrum emitted by the generated plasma and to convey it towards the optical spectrometer.

12. The gas analysis system of claim 11, wherein the optical fiber has one end inside the vacuum pumping line.

13. The gas analysis system of claim 10, wherein the vacuum pumping line is upstream of the process chamber.

14. A gas analysis system for analyzing gases in a vacuum pumping line of a process chamber, said analysis system comprises apparatus for ionizing the gases to be analyzed, and apparatus for analyzing the ionized gases, wherein:

the apparatus for ionizing the gases to be analyzed comprises a dedicated plasma source, inside the vacuum pumping line and in contact with the gases contained in the vacuum pumping line, and a generator for generating a plasma from the gases to be analyzed, further wherein the plasma source is a radio frequency plasma source of the inductively coupled plasma type, the generator is an RF generator, and a dielectric, made of one of quartz and alumina, provides sealing and is transparent to electromagnetic waves; and the apparatus for analyzing the ionized gases comprises a radiation sensor situated in the vicinity of the zone in which the plasma is generated, and connected to an optical spectrometer for analyzing variation of the radiation spectrum emitted by the generated plasma.

15. The gas analysis system of claim 14, wherein the vacuum pumping line is upstream of the process chamber.

\* \* \* \* \*